US007115887B1

(12) United States Patent
Hassanein et al.

(10) Patent No.: US 7,115,887 B1
(45) Date of Patent: Oct. 3, 2006

(54) METHOD FOR GENERATING EXTREME ULTRAVIOLET WITH MATHER-TYPE PLASMA ACCELERATORS FOR USE IN EXTREME ULTRAVIOLET LITHOGRAPHY

(75) Inventors: Ahmed Hassanein, Bolingbrook, IL (US); Isak Konkashbaev, Bolingbrook, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 11/079,238

(22) Filed: Mar. 15, 2005

(51) Int. Cl.
*A61N 5/06* (2006.01)
*G01J 3/10* (2006.01)
*H05G 2/00* (2006.01)

(52) U.S. Cl. .................................................. 250/504 R

(58) Field of Classification Search ..................... None
See application file for complete search history.

(56) References Cited

U.S. PATENT DOCUMENTS 3,997,468 A * 12/1976 Maljushevsky et al. ........ 516/9
4,042,848 A * 8/1977 Lee ............................ 376/145
4,494,043 A * 1/1985 Stallings et al. ........ 315/111.41

* cited by examiner

*Primary Examiner*—Jack Berman
*Assistant Examiner*—Jennifer Yantorno
(74) *Attorney, Agent, or Firm*—Mark LaMarre; Mark P. Dvorscak; Paul A. Gottlieb

(57) ABSTRACT

A device and method for generating extremely short-wave ultraviolet electromagnetic wave uses two intersecting plasma beams generated by two plasma accelerators. The intersection of the two plasma beams emits electromagnetic radiation and in particular radiation in the extreme ultraviolet wavelength. In the preferred orientation two axially aligned counter streaming plasmas collide to produce an intense source of electromagnetic radiation at the 13.5 nm wavelength. The Mather type plasma accelerators can utilize tin, or lithium covered electrodes. Tin, lithium or xenon can be used as the photon emitting gas source.

10 Claims, 5 Drawing Sheets

MATHER'S TYPE PLASMA ACCELERATOR

MATHER'S TYPE PLASMA ACCELERATOR

MATHER'S TYPE PLASMA ACCELERATOR

Figure 1:
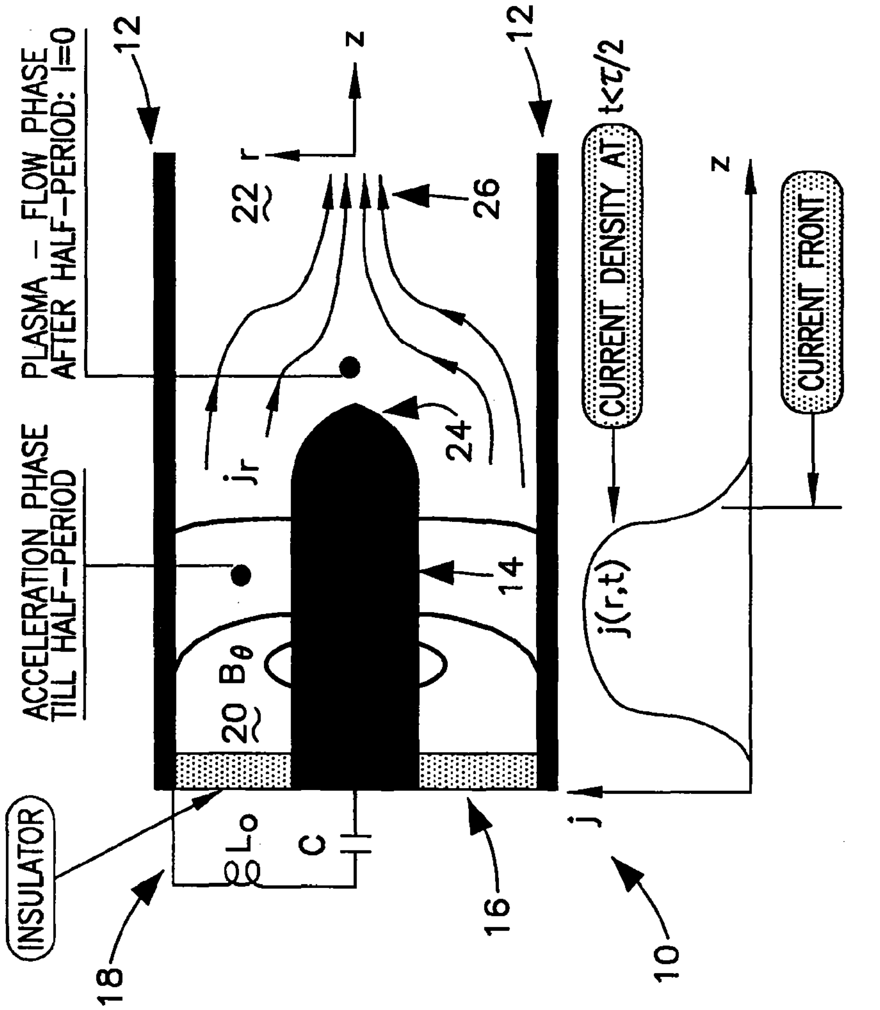

COLLISION OF COUNTERSTREAMING PLASMAS
IN GUIDE MAGNETIC FIELD TO HOT PLASMA FORMATION

COLLISION OF COUNTERSTREAMING PLASMAS
IN GUIDE MAGNETIC FIELD TO HOT PLASMA FORMATION

SCHEMATIC VIEW OF A DPF DEVICE

METHOD FOR GENERATING EXTREME ULTRAVIOLET WITH MATHER-TYPE PLASMA ACCELERATORS FOR USE IN EXTREME ULTRAVIOLET LITHOGRAPHY

CONTRACTUAL ORIGIN OF INVENTION

The United States Government has rights in this invention pursuant to Contract No. W-31-109-ENG-38 between the U.S. Department of Energy and the University of Chicago representing Argonne National Laboratory.

FIELD OF THE INVENTION

The present invention relates to an improvement in Extreme Ultraviolet Lithography (EUVL). More specifically this invention relates to a method and apparatus for producing the 13.5 nm wavelength radiation for Extreme Ultra Violet Lithography (EUVL).

BACKGROUND OF THE INVENTION

Description of Related Art

The current process for chip making is called deep-ultraviolet lithography (DUV), which is a photography-like technique that focuses light through lenses to expose the raw circuit material and the accompanying photomask. Subsequent etching and chemical processing carves circuit patterns on the circuit material, such as a silicon wafer. The key to creating more compact and powerful microprocessors is the size of the light's wavelength. The shorter the wavelength of light that is used, the more transistors that can be etched onto a given area of a silicon wafer's surface. As of 2001, deep-ultraviolet lithography used a wavelength of 230 nanometers (nm) and it is anticipated that that DUV technology will permit features as small at about 100 nm. The next generation of lithography under development is known as Extreme Ultraviolet Lithography (EUVL).

EUVL uses a light source with a wavelength of 13.5 nanometers (nm). This wavelength may be obtained from plasma-based systems using a variety of technological approaches. In U.S. Pat. No. 6,493,423, a plasma generating gas is exposed to a high energy pulsed laser producing extreme ultra violet radiation (EUV) in the desired range. The plasma-generating gas may be a gas such as xenon. When the laser hits the xenon gas, the laser heats the gas up and creates plasma. Once the gas is plasmatized, electrons are emitted from the plasma and the plasma radiates light at 13.5 nm. The problem with creating the plasma by means of a laser is that lasers of sufficient power are expensive, both to purchase and to operate. It order to develop EUVL commercially, is will be necessary to provide an inexpensive source of plasma.

For many years, it has been known that x-rays and high energy ultraviolet radiation could be generated by a plasma source referred to as z-pinch. In a z-pinch plasma source an electric current passes between two electrodes, through a plasma generating gas, in one of several possible configuration. The magnetic field created by the flowing electric current accelerates the electrons and ions in the plasma into a tiny volume with sufficient energy to cause substantial stripping of outer electrons from the ions and a consequent production of x-rays and high energy ultraviolet radiation. Typical prior art plasma z-pinch devices, such as presented in Asmus et al., U.S. Pat. No. 4,889,605 and Stromberg et al., U.S. Pat. No. 4,899,355, can generate large amounts of radiation suitable for proximity x-ray lithography. However, these devices are limited in repetition rate due to large per pulse electrical energy requirements, and short lived internal components. The stored electrical energy requirements for these systems range from 10 to 20 Joules(J)/pulse The repetition rates typically did not exceed a few pulses per second. Further, the problem with electrodes, in the plasma environment, is that electrodes, particularly the anode, suffer from a high erosion rate due to particle and heat fluxes resulting in low efficiency and short lifetimes of the electrodes and optical components.

One of the main obstacles now in achieving EUVL commercial goals in discharge produced plasma (Hereinafter referred to as "DPP") devices is electrode erosion at the required high power necessary for high volume manufacturing (Hereinafter referred to as "HVM"). Only in recent years has there been research from various groups to develop devices to obtain 100–200 W radiation sources and now meet a serious problem with material erosion. This is due to the very small efficiency, $\zeta$ to transfer stored energy in 13.5 nm radiation: as $\zeta \approx 0.1$–1% the required electric power should be about 100 kW. If the plasma-facing component (PFC) surface has an area less 100 $cm^2$ the heat load on the surrounding surfaces exceeds 1 $kW/cm^2$ which is difficult to remove by conventional methods as it is well studied in fusion reactor and space research investigations.

SUMMARY OF THE INVENTION

An object of this invention is to provide a method and apparatus for generating electromagnetic radiation in the range of 13.5 nm that does not degrade or erode the electrode material.

These and other objectives of the invention, which will become apparent from the following description, have been achieved by a novel method and apparatus for generating/producing extremely short-wave ultraviolet electromagnetic wave radiation, comprising: wave front zone; a plasma generating gas within the wave front zone; a first plasma accelerator source having an anode and a cathode thereby being adapted to form a first plasma generating zone and producing a first plasma beam; a second plasma accelerator source having a second anode and a second cathode thereby being adapted to form a second plasma generating zone and producing a second plasma beam; wherein the second plasma beam intersects the first plasma beam within the wave front zone at an angle of intersection $\hat{\alpha}$, wherein the angle $\hat{\alpha}$ is from 90° to 180° and the intersecting plasma beams within the wave front zone emits electromagnetic radiation at a wavelength from about 10 nm to about 20 nm, and preferably, 13.5 nm. Preferably the angle $\hat{\alpha}$ is 180 so that the two plasma accelerators oppose one another and the plasma streams produce by the plasma accelerators collide. Preferably, the first plasma beam and the second plasma beam are opposed and axially aligned.

The plasma generating gas is selected from the group consisting of xenon, vaporized tin and vaporized lithium. The first anode or the second anode is coated with a metal, the metal selected from the group consisting of tin and lithium. The plasma accelerators and the resulting plasmas are generated at a temperature from about 20 eV to about 40 eV. Typically, the potential difference between the anode and cathode is from about 10 kV to about 50 kV.

The preferred device for generating/producing extremely short-wave ultraviolet electromagnetic wave radiation, comprising: a wave front zone; a plasma generating gas within the wave front zone; a first plasma accelerator source having an anode and a cathode thereby being adapted to form a first plasma generating zone and producing a first plasma beam; a second plasma accelerator source having a second anode and a second cathode thereby being adapted to form a second plasma generating zone and producing a second plasma beam; wherein the first plasma beam and the second plasma beam oppose one another and are axially aligned and the first plasma beam intersects the second plasma beam within the wave front zone and the intersecting plasma beams within the wave from zone emit electromagnetic radiation at a wavelength from about 10 nm to about 20 nm.

A method for generating/producing extremely short-wave ultraviolet electromagnetic wave, comprising: providing a wave front zone; providing a plasma generating gas within the wave front zone; providing a first plasma accelerator source having an anode and a cathode thereby being adapted to form a first plasma generating zone and producing a first plasma beam; providing a second plasma accelerator source having a second anode and a second cathode thereby being adapted to form a second plasma generating zone and producing a second plasma beam; wherein the second plasma beam intersects the first plasma beam within the wave front zone at an angle of intersection $\hat{\alpha}$, wherein the angle $\hat{\alpha}$ is from 90° to 180° and the intersecting plasma beams within the wave from zone emits electromagnetic radiation at a wavelength from about 10 nm to about 20 nm.

BRIEF DESCRIPTION OF THE SEVERAL VIEWS OF DRAWINGS

Figure 2:
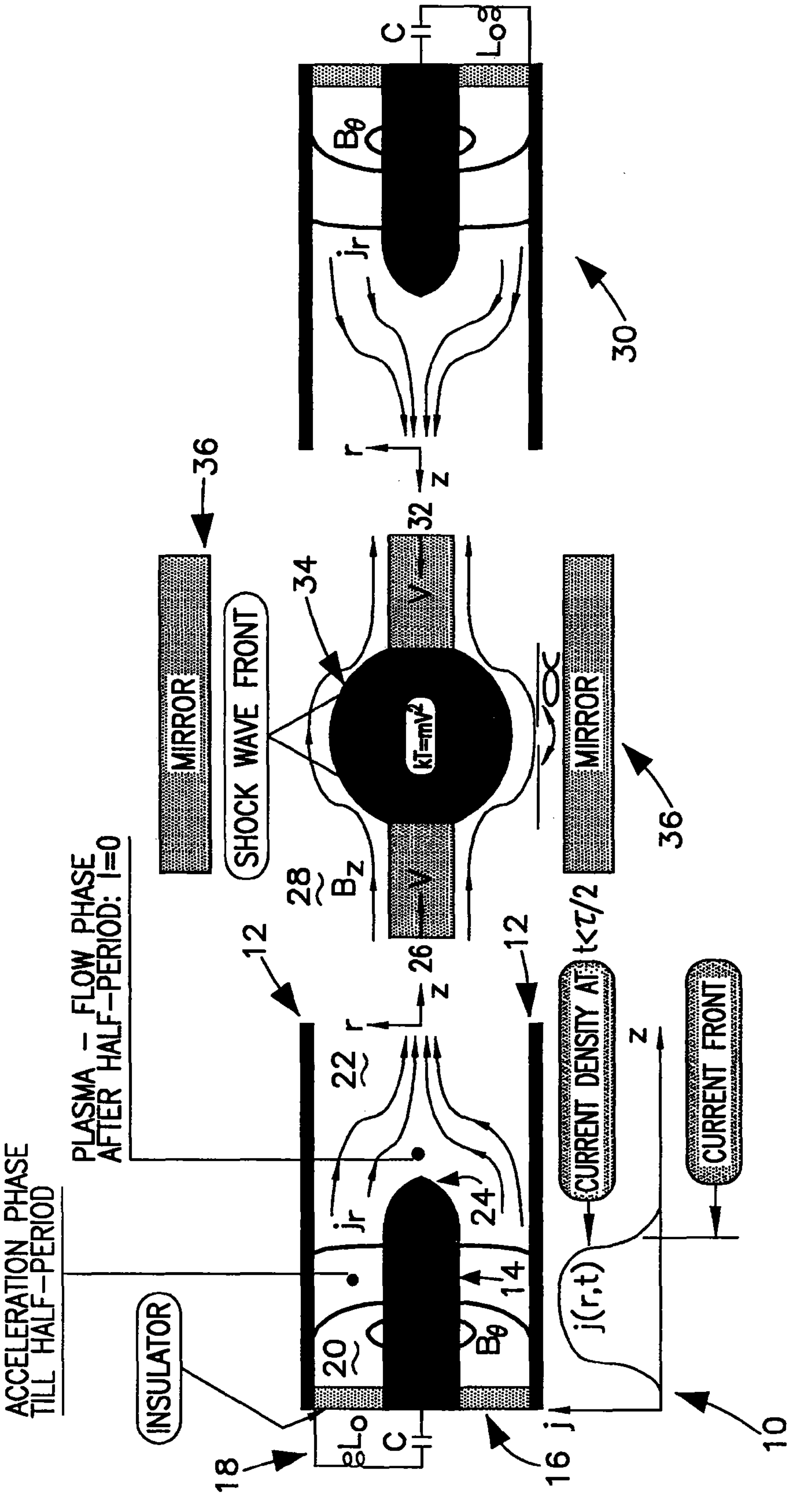

With this description of the invention, a detailed description follows with reference being made to the accompanying figures of drawings which form part of the specification, in which like parts are designated by the same reference numbers, and of which:

FIG. 1 is a schematic of a Mather-type plasma accelerator for use with this invention, FIG. 2 is a schematic illustration of twin Mather-type plasma accelerator for use with this invention in opposed configuration.

Figure 3A:
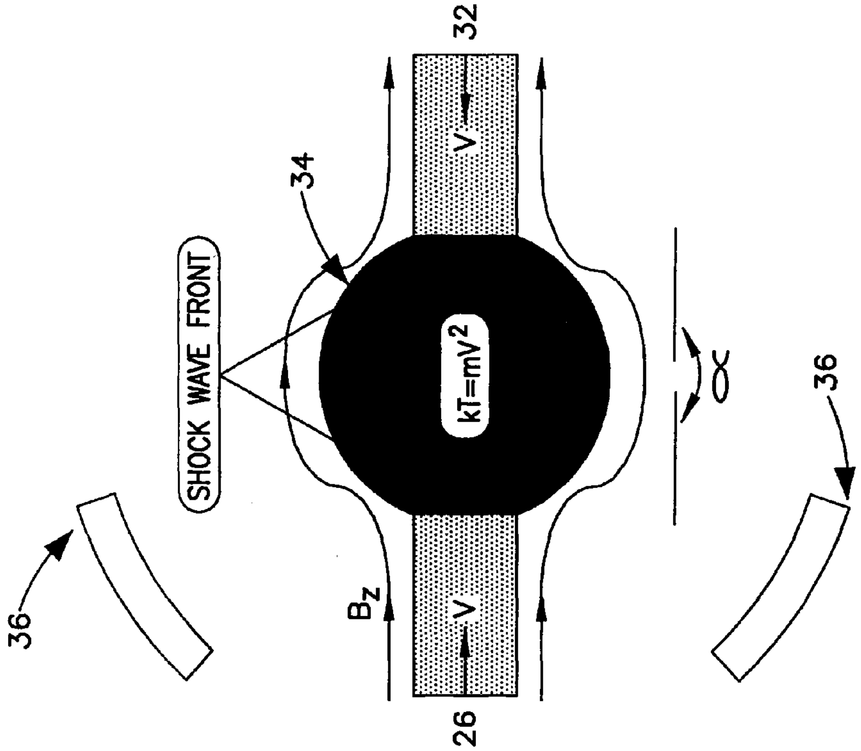
Figure 3B:
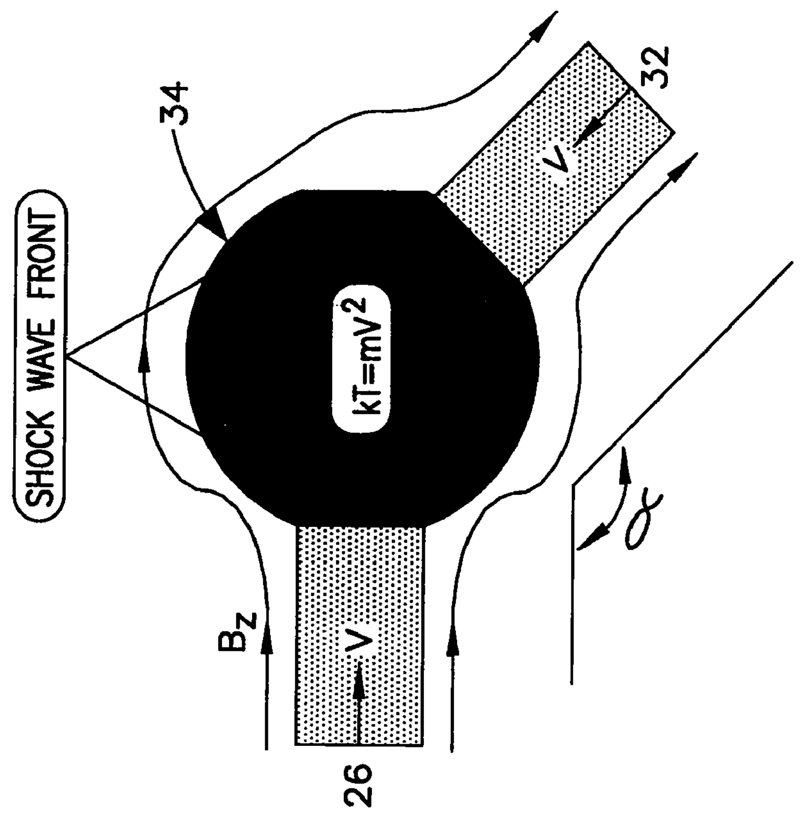
Figure 4:
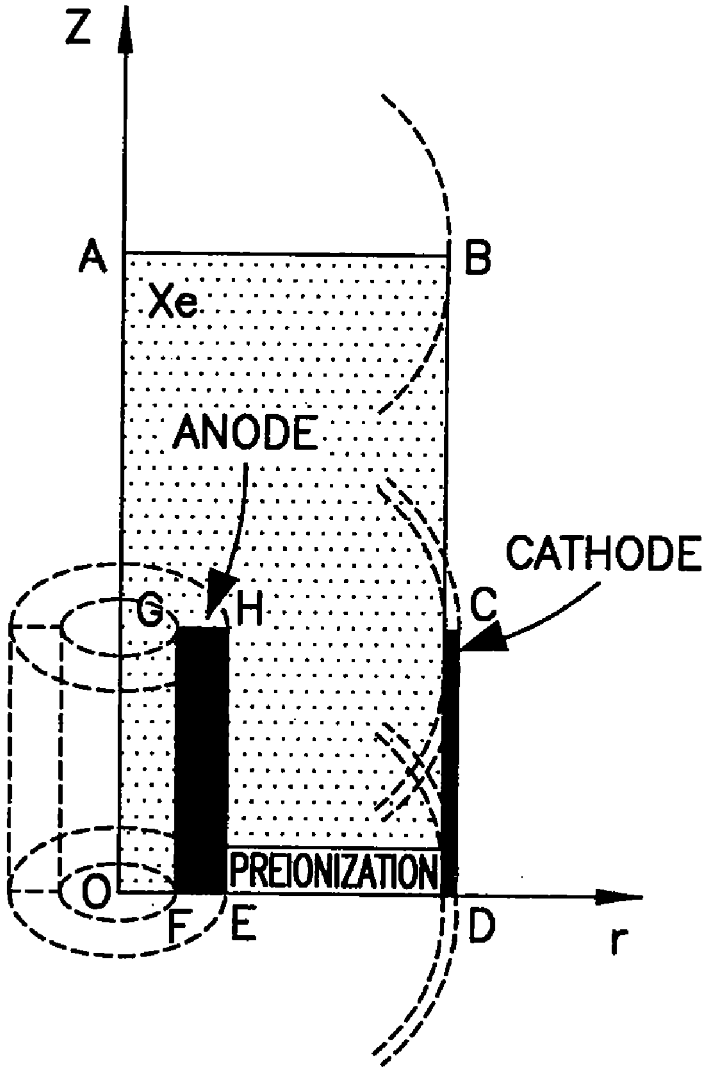

FIGS. 3*a* and 3*b* are schematic illustrations of the collision of two plasma sources in different orientation to illustrate the variability on collision angles and alternate mirror configurations FIG. 4 is a schematic view of a DPF device.

FIGS. 5*a* and 5*b* are Absorption of Xe plasma at temperature of 30 eV, density $10^{16}$ $cm^{-3}$ with line splitting (right) and without splitting (left).

The invention is not limited in its application to the details and construction and arrangement of parts illustrated in the accompanying drawings since the invention is capable of other embodiments that are being practiced or carried out in various ways. Also, the phraseology and terminology employed herein are for the purpose of description and not of limitation.

DETAILED DESCRIPTION OF THE INVENTION

A plasma accelerator for use with this invention is shown generally at 10 in FIG. 1. This plasma accelerator is referred to as a Mather's type accelerator. The plasma accelerator comprises cathodes 12 and typically a central anode 14 electrically isolated from one another by insulator 16. Circuit 18 provides power to the anode 14 and cathodes 12. The initial phase in which the voltage pulse is applied across the electrodes when a spark gap is triggered breaks down over the insulator 16. A current front is formed and the plasma (ions and electrons) lifts off from the cathode 12. The current sheath moves down the length of the cathode 12. The motion is caused by the J×B force where J is the current vector that goes down the cathode 12, across the gap 20, and up the inner electrode (assuming a positive outer electrode). The resulting magnetic field, $B_\theta$, encircles the inner electrode and the force applied to the plasma, F, is directed to the cathode opening 22. During the rundown phase, the plasma front will accelerate to a velocity on the order of $10^7$ cm/sec and the discharge current may reach levels in excess of 100 kA. When the current reaches the end of the anode 14 it collapses toward the axis due to the geometry of the magnetic field. This collapse creates a small region of high density plasma just beyond the end 24 of the center anode 14. This phase is sometimes more dramatically described as the radical pinch phase.

As the current J and plasma stream 26 composed of ions and electron accelerate in direction z the stream 26 extends past the end of cathode 12 and enters the wave front zone 28, as shown in FIG. 2. FIG. 2 illustrates the preferred arrangement of multiple plasma accelerators 10 and 30 for use with this invention. The wave front zone 28 contains a suitable gas, such as xenon, vaporized tin or vaporized lithium. Plasma streams 26 and 32 from plasma accelerators 10 and 30 respectively enter the wave front zone 28. The two plasmas 26 and 32 collide at angle $\hat{\alpha}$ at shock wave front 34 and emit electromagnetic radiation $\lambda$ in the extreme ultraviolet range, within the required range of wavelengths and preferably within the range of from about 10 nm to about 20 nm and more specifically at a wavelength of about 13.5 nm. Due to the nature of plasmas, electromagnetic radiation outside of the preferred range of wavelengths may also be emitted. Mirrors 36 collect and focus the electromagnetic radiation of the desired wavelength. Although the mirrors are shown parallel to the shock wave front 34 for this illustration, the mirrors may be shaped or angled as required to direct the electromagnetic radiation of the necessary wavelength. Alternative plasma orientations and mirror arrangements are shown in FIGS. 3*a* and 3*b*.

The angle $\hat{\alpha}$ of collision for the two plasma streams 26 and 32 is from about 90° to about 180°. The preferred orientation for the two plasma accelerators as shown in FIG. 2 utilizes two axially aligned plasma accelerators where the two beams collide at an angle $\hat{\alpha}$ of about 180°. Based on the geometry of the device and design considerations, it may be necessary to have the two plasma beams collide at an angle $\hat{\alpha}$ other than 180°.

The magnetic field $B_\theta$required to generate the temperature and currents of the this device is typically on the order of from about 7.5 kilo Gauss (kG) to about 10 kG (One Tesla). The current J to generate a magnetic field of the magnitude is from about 20 kA to about 50 kA. The potential difference across the electrodes is from about 10 kV to about 100 kV and preferably from about 30 kV to about 50 kV. The pulse duration applied is from about 100 nanoseconds to about 500 nanoseconds. The resulting plasmas 26 and 32 exist at temperatures from about 20 eV to about 40 eV. The plasma generating gas is typically maintained at a density of from about $10^{17}$ to about $10^{18}$ atoms/$cm^3$. The hot plasma 26 generated by the magnetic field created by the flowing electric current accelerates the electrons and ions in the plasma into a tiny volume with sufficient energy to cause substantial stripping of outer electrons from the ions and a consequent production of x-rays and high energy ultraviolet radiation. The extremely short-wave ultraviolet electromagnetic wavelength light (EULV) produced by this device is from about 10 nm to about 20 nm and preferably about 13.5 nm. Mirrors 36, as shown in FIG. 2 direct and focus the extreme short-wave ultraviolet electromagnetic wavelength light, which is then directed to the material to be exposed (Not Shown). Mirrors in FIG. 2 are only shown schematically. Actual arrangement of mirrors is determined by the numerous design requirements, such as the need to diminish various debris fluxes to the surfaces of the very expensive multi-layer mirrors. One of possible designs is to collide two counter-streaming plasma flows from accelerators inside the open trap of stable magnetohydrodynamic cusp geometry where hot plasma escapes the trap along its openings (two point opening and one circular opening).

The plasma accelerators 10 and 30 are fabricated with electrodes made from materials such as molybdenum, tungsten, copper or alloys of combinations of these metals. The electrodes may be coated with tin or lithium if vaporized forms of these metals are used for the plasma generating gases. The insulators are formed from any suitable insulating material such as silicon nitride or boron nitride (PBN)

Mathematical Model

A general magnetohydrodynamic (MHD) device is shown in FIG. 5. The electrodes are shown in dark color and are of equal height. The device is filled by radiating (xenon, tin or lithium) gas under an initial pressure in the range of several tens of mtorr at room temperature, corresponding to an initial density of the gas in the range of $10^{14}$–$10^{15}$ $cm^{-3}$. It is also assumed that a preionization step that heats the gas to a temperature of ≈1 eV occurs near the bottom of the device.

We solve the general set of three-dimensional (3-D) resistive conservative MHD equations contain the description of the behavior of conductive flow in the magnetic field due to current displacement triggered by the discharge. The processes of all magnetic diffusion and radiation energy loss are included.

$$\frac{\partial \rho}{\partial t} + \nabla\cdot(\rho v) = 0, \tag{2.1}$$

$$\frac{\partial \rho v}{\partial t} + \nabla\cdot\left(\rho vv + p_{tot} - \frac{1}{4\pi}BB\right) = 0, \tag{2.2}$$

$$\frac{\partial e_{tot}}{\partial t} + \nabla\cdot\Bigg[v(e_{tot}+p_{tot}) - \frac{1}{4\pi}(v\cdot B)B + \frac{c^2\eta}{16\pi^2}(\nabla\times B)\times B - \chi\nabla T - S_{rad}\Bigg] = 0, \tag{2.3}$$

$$\frac{\partial B}{\partial t} + \nabla\cdot(vB - Bv) + \frac{c^2}{4\pi}\nabla\times(\eta\nabla\times B) = 0. \tag{2.4}$$

Equations 2.1–2.4 represent, in Gaussian units, the conservation of mass, momentum, energy, and magnetic flux, respectively. The plasma is described by the conservative variables of mass density ρ, momentum density ρv, total energy density e, and magnetic field B. In the rest of the paper, the magnetic permeability μ is assumed to be 1. Total energy density is determined as a sum of internal, kinetic, and magnetic energy densities, whereas the pressure term is separated into hydrodynamic and magnetic parts:

$$e_{tot} = e_h + \frac{B^2}{8\pi} = e_{int} + \frac{\rho v^2}{2} + \frac{B^2}{8\pi}, \tag{2.5}$$

-continued $$p_{tot} = p_h + \frac{B^2}{8\pi}.$$

To complete this full system of MHD equations, thermodynamic pressure $p_h = p_h(e_{int}, \rho)$, resistivity $\eta = \eta(e_{int}, \rho)$, and thermal conductivity $X = X(e_{int}, \rho)$ functions are calculated from the equation of state, discussed below.

Applying cylindrical symmetry of a plasma focus device, we wrote the general set of MHD equations (2.1–2.4) in axisymmetrical cylindrical geometry (r, ϕ, z). We neglect the plasma motion in the ϕ direction and assume that magnetic field has only one component Bϕ. Therefore, to simplify the expressions, subscript ϕ is further omitted from the magnetic field term.

In coordinate formulation, the general set may be written as $$\frac{\partial U}{\partial t} + \frac{1}{r}\frac{\partial}{\partial r}[rF(U)] + \frac{\partial P(U)}{\partial r} + \frac{\partial G(U)}{\partial z} = \Omega, \tag{2.6}$$

where $$U = \begin{bmatrix} \rho \\ \rho v^r \\ \rho v^z \\ e_{tot} \\ B \end{bmatrix},\quad F(U) = \begin{bmatrix} \rho v^r \\ \rho v^r v^r \\ \rho v^z v^r \\ v^r(e_{tot}+p_{tot}) - \frac{c^2\eta B}{16\pi^2 r}\left[\frac{\partial}{\partial r}(rB)\right] - \chi\frac{\partial T}{\partial r} \\ 0 \end{bmatrix},$$

$$P(U) = \begin{bmatrix} 0 \\ p_{tot} \\ 0 \\ 0 \\ v^r B - \frac{c^2\eta}{4\pi r}\frac{\partial rB}{\partial r} \end{bmatrix},\quad \Omega = \begin{bmatrix} 0 \\ -\frac{B^2}{4\pi r} \\ 0 \\ Q_{rad} \\ 0 \end{bmatrix},$$

$$G(U) = \begin{bmatrix} \rho v^z \\ \rho v^r v^z \\ \rho v^z v^z + p_{tot} \\ v^z[e_{tot}+p_{tot}] - \frac{c^2\eta B}{16\pi^2}\frac{\partial B}{\partial z} - \chi\frac{\partial T}{\partial z} \\ v^z B - \frac{c^2\eta}{4\pi}\frac{\partial B}{\partial z} \end{bmatrix},$$

and the solution of U entirely defines the state of the system.

The conservative form of the initial equations allows the use of the TVD method in Lax-Friederich formulation (TVD-LF) for the numerical solution of the system. A second-order TVD-LF scheme can be applied to the system of conservation laws that does not use either a Riemann solver or the characteristic wave solution. Matrix formalism enables us to change the governing equations (2.6) without significantly modifying the method. For example, to calculate a two-gas mixture approximation, it is necessary to add the second continuity equation and extend the elements of matrixes to six terms.

To calculate the radiation heat flux, the radiation transport equation (RTE), which presents the energy conservation law for the total radiative intensity S must be solved. In this study, we utilized the discrete-ordinates method, which varies the radiative intensity along specified directions. The RTE is thus solved for a set of discrete directions that span the total spherical solid angle of 4π.

At each point of the MHD zone, local temperature T, the Plank function $I_p$ and optical coefficients $k_{emi}$, and $k_{abs}$ of emission and absorption of the photon with energy E define the specific intensity of radiation. In the case of axisymmetric cylindrical coordinates (r, z), the RTE for intensity $I_E$ can be written along the direction s as $$\frac{dI_E}{ds} = \sin\theta\left(\mu\frac{\partial I}{\partial r} + \frac{1-\mu^2}{r}\frac{\partial I_E}{\partial \mu}\right) + \cos\theta\frac{\partial I_E}{\partial z} = \kappa_{emi} I_P - \kappa_{abs} I_E. \quad (2.7)$$

Here, θ is the angle between the direction of the ray s and the z-axis, ϕ is the angle between the projection of the direction s to the plane, perpendicular to z and normal to the cylindrical surface, and μ=cost ϕ. The intensity in direction s is calculated by integration over all of the photon frequencies. Net flux $s_{rad}$ is obtained by integrating over all of the angles:

$$S_{rad} = \int\left[\int_0^{2\pi}\delta\varphi\int_0^{\pi} I_E(\theta, \varphi)\chi o\sigma\theta\sigma i v\theta\delta\theta\right]dE. \quad (2.8)$$

The radiation energy loss in each cell is then found from $Q_{rad}=\nabla\cdot S_{rad}$. Essentially, this method is the result of finite differencing of the directional dependence of the RTE. Integrals over solid angles are approximated by numerical quadrature, the choice of which defines the directions of the RTE. The solution is carried out simultaneously with the solution of energy balance to provide the distribution of the local energy source, temperature, and density profile.

The calculation of thermodynamic and optical plasma characteristics is performed in several steps, which are described in more detail in the section on atomic and opacities data.

Boundary Conditions

To simulate various possible effects that occur in the boundaries of the EUV source, we have considered several methods of stating these effects in the form of boundary conditions. In simplified form, one may subdivide these conditions into two major parts. A hydrodynamic part includes the conditions applied to hydrodynamic flow in the area or near the boundaries. Magnetic field conditions manage the behavior of the current and the magnetic field near the surfaces of the device. In the discussion below, we refer the reader to FIGS. 5*a* and 5*b*.

Hydrodynamic boundary conditions:

rigid wall boundary: $F_n|_b=0$, where $F_n$ is normal to the boundary component of hydrodynamic flux. Such a condition is applied at the cathode and anode surfaces |GF|, |GH|, |HE| and |CD| to set up the absence of flow passing through the boundary;

Z-axis symmetry: $\rho v_0^r=-\rho v_1^r$, $\rho v_{-1}^r=-\rho v_2^r$. A mirrorlike condition is stated in |OA| that there is no radial hydrodynamic flow on the Z axis.

Magnetic field initial and boundary conditions:

driving magnetic field: applied in |ED| as $$B = \frac{2I}{cr},$$

where I is the total current of the device, r is the upper radius, c is the speed of light;

conducting solid wall without surface current:

$$\frac{\partial(rB)}{\partial r} = 0.$$

This condition states that the current is concentrated at the surface of a conductor and is applied at the surface of the cathode |CD| and the internal surface of the anode |GF|;

ideal conducting wall, total current flows at the surface: B=0. As above, this condition states that total current is concentrated at the external surface of the conductor, and is applied on the external surface of the anode |HE|.

Z-axis symmetry: $B|_{r=0}=0$. The symmetry of the domain defines the symmetry of the magnetic field.

Thus, in accordance with the invention, there has been provided a method and apparatus for generating electromagnetic radiation in the range of 13.5 nm that does not degrade or erode the electrode material is needed.

With this description of the invention in detail, those skilled in the art will appreciate that modification may be made to the invention without departing form the spirit thereof. Therefore, it is not intended that the scope of the invention be limited to the specific embodiments that have been illustrated and described. Rather, it is intended that the scope to the invention be determined by the scope of the appended claims.

We claim:

1. A device for generating/producing extremely shortwave ultraviolet electromagnetic wave radiation, comprising:

a wave front zone;

a plasma generating gas within the wave front zone;

a first plasma accelerator source having an anode and a cathode thereby being adapted to form a first plasma generating zone and producing a first plasma beam;

a second plasma accelerator source having a second anode and a second cathode thereby being adapted to form a second plasma generating zone and producing a second plasma beam;

wherein the second plasma beam intersects the first plasma beam within the wave front zone at an angle of intersection ά, wherein the angle ά is from 90° to 180° and the intersecting plasma beams within the wave front zone emits electromagnetic radiation at a wavelength from about 10 nm to about 20 nm.

2. The device for generating/producing extremely shortwave ultraviolet electromagnetic wave of claim 1, wherein the angle ά is 180.

3. The device for generating/producing extremely shortwave ultraviolet electromagnetic wave of claim 1, wherein the plasma generating gas is selected from the group consisting of xenon, vaporized tin and vaporized lithium.

4. The device for generating/producing extremely shortwave ultraviolet electromagnetic wave of claim 1, wherein the first anode or the second anode are coated with a metal selected from the group consisting of tin and lithium.

5. The device for generating/producing extremely short-wave ultraviolet electromagnetic wave of claim 1, wherein the first plasma beam and the second plasma beam are opposed and axially aligned.

6. The device for generating/producing extremely short-wave ultraviolet electromagnetic wave of claim 1 wherein plasma is generated at a temperature from about 20 eV to about 40 eV.

7. The device for generating/producing extremely short-wave ultraviolet electromagnetic wave of claim 1 wherein the extremely short-wave ultraviolet electromagnetic wavelength is about 13.5 nm.

8. The device for generating/producing extremely short-wave ultraviolet electromagnetic wave of claim 1, wherein the potential between the cathode and anode is from about 10 kV and 50 kV.

9. A device for generating/producing extremely short-wave ultraviolet electromagnetic wave radiation, comprising:

a wave front zone;

a plasma generating gas within the wave front zone;

a first plasma accelerator source having an anode and a cathode thereby being adapted to form a first plasma generating zone and producing a first plasma beam;

a second plasma accelerator source having a second anode and a second cathode thereby being adapted to form a second plasma generating zone and producing a second plasma beam;

wherein the first plasma beam and the second plasma beam oppose one another and are axially aligned and the first plasma beam intersects the second plasma beam within the wave front zone and the intersecting plasma beams collide within the wave front zone emit electromagnetic radiation at a wavelength from about 10 nm to about 20 nm.

10. A method for generating/producing extremely short-wave ultraviolet electromagnetic wave, comprising: providing a wave front zone;

providing a plasma generating gas within the wave front zone;

providing a first plasma accelerator source having an anode and a cathode thereby being adapted to form a first plasma generating zone and producing a first plasma beam;

providing a second plasma accelerator source having a second anode and a second cathode thereby being adapted to form a second plasma generating zone and producing a second plasma beam;

wherein the second plasma beam intersects the first plasma beam within the wave front zone at an angle of intersection a, wherein the angle $\acute{\alpha}$ is from 90° to 180° and the intersecting plasma beams within the wave from zone emits electromagnetic radiation at a wavelength from about 10 nm to about 20 nm.

* * * * *